(12) United States Patent
Bergin et al.

(10) Patent No.: US 8,690,875 B2
(45) Date of Patent: Apr. 8, 2014

(54) METHOD AND APPARATUS FOR PREPARING BONE FOR A PROSTHETIC DEVICE

(75) Inventors: Alisha W. Bergin, Southaven, MS (US); Jerry L. Jones, Memphis, TN (US); Richard D. Lambert, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 345 days.

(21) Appl. No.: 12/681,106

(22) PCT Filed: Oct. 1, 2008

(86) PCT No.: PCT/US2008/078470
§ 371 (c)(1),
(2), (4) Date: Mar. 31, 2010

(87) PCT Pub. No.: WO2009/046121
PCT Pub. Date: Apr. 9, 2009

(65) Prior Publication Data
US 2010/0217267 A1    Aug. 26, 2010

Related U.S. Application Data

(60) Provisional application No. 60/976,717, filed on Oct. 1, 2007, provisional application No. 60/976,697, filed on Oct. 1, 2007.

(51) Int. Cl.
*A61B 17/56* (2006.01)
*A61B 17/58* (2006.01)
*A61F 2/30* (2006.01)
*A61B 17/00* (2006.01)
*A61F 2/46* (2006.01)

(52) U.S. Cl.
USPC .......................................... 606/80; 606/86 R (58) Field of Classification Search
USPC .................................................. 606/80, 86 R
See application file for complete search history.

(56) References Cited

U.S. PATENT DOCUMENTS

| | | | | |
|---|---|---|---|---|
| 6,117,138 A | * | 9/2000 | Burrows et al. | 606/80 |
| 7,235,106 B2 | | 6/2007 | Daniels et al. | |
| 2004/0267266 A1 | * | 12/2004 | Daniels et al. | 606/80 |
| 2011/0112540 A1 | | 5/2011 | McLean et al. | |

OTHER PUBLICATIONS

Japanese Patent Office, Japanese Second Office Action dated Dec. 24, 2013, 5 pages.

* cited by examiner

*Primary Examiner* — David Bates
(74) *Attorney, Agent, or Firm* — David A. Chambers (57) ABSTRACT

A system (10) for preparing a long bone for a prosthetic, the long bone having a long axis comprises a distal instrument (12) and a proximal instrument (14). The distal instrument (12) is configured to remove bone from a distal portion of bone. The distal instrument (12) has a bone removing portion (16) configured to remove bone along the long axis of the long bone and a shaft (18) extending from the bone removing portion (16) along the long axis of the long bone. The proximal instrument (14) is configured to overlie the shaft (18) of the distal element (12) within the long bone. The distal shaft (18) guides the proximal instrument (14) to prepare the proximal portion of the long bone after the distal instrument (12) has prepared the distal portion of the long bone.

53 Claims, 8 Drawing Sheets

METHOD AND APPARATUS FOR PREPARING BONE FOR A PROSTHETIC DEVICE

CROSS-REFERENCE TO RELATED APPLICATIONS

This application is a U.S. National Phase filing of International Application No. PCT/US2008/078470 which claims the benefit of U.S. Provisional Application No. 60/976,717, filed Oct. 1, 2007 and U.S. Provisional Application No. 60/976,697, filed Oct. 1, 2007. The disclosure of each application is incorporated by reference in its entirety.

BACKGROUND OF THE INVENTION

1. Field of the Invention

This invention relates generally to hip surgeries and, more particularly, relates to surgical methods and tools for preparing a femur and trialing the femur for an implant.

2. Related Art

Most modular systems require instrumentation comprising distal stem trials, proximal sleeve trials, proximal body segment trials, and trial necks to replicate the implant. An implant is then selected based on the trial instrumentation that provides the best fit for the patient. Using distal stem trials adds to the number of instruments in system, therefore increasing inventory overhead and cost of manufacture. More instruments may also lead to confusion in the OR, and a larger cleanup/sterilization operation. There is also a need to simplify instrumentation in such a way that surgical assistants are not burdened by handling large, heavy instrument sets.

With conventional systems, a surgeon must remove distal reamers from the femoral canal and replace them with a distal stem trial connected to a proximal stem trial. Each time a reamer is removed and a distal stem trial is inserted in its place, there are risks of fracture and/or excessive bone removal, because the distal stem trial adds an additional scratch-fit step. In cases of poor bone quality, these risks may be substantially increased. In addition to an increased risk of fracture for each reamer removal step, there is also an increased OR time for the surgeon. The time it takes to ream the femoral canal, remove the reamer from the femoral canal, and implant a distal stem trial can be costly.

The present invention is more advantageous than conventional methods, because the distal reamer serves two purposes instead of one, thereby reducing the number of steps and parts needed to perform the same surgical procedure. The distal reamer is first used to distally ream the femoral canal, and then it is left in place within the canal. The distal reamer is configured to allow a proximal trial and trial neck assembly to be connected to it in such a way that trial reduction may be performed immediately after the distal reamer has stopped cutting. Modular neck segments of the present invention allow quick trial reduction with the reamer still within the femoral canal. By trialing off of the reamer, the present invention avoids a set of separate stem trials.

The standard practice for implanting a hip system is to prepare the bone using a first set of instruments, and then perform a trial reduction using a second set of instruments that is different from the first set. Conventionally, reamers clear a passage within a femoral canal, and then a trial stem is selected from a kit and inserted into said passage. Trial reduction takes place using the trial stem. After the joint is reduced, the trial stem is removed from the femoral canal and then replaced with the correspondingly sized implant stem. This standard practice generally takes more time to perform and is less efficient than the present invention, because more instruments and method steps are needed to carry out the same procedure. More time in the OR means exposing patients to more risk, and increasing hospital overhead. Another practice for implanting a hip system is to prepare the bone using a first set of instruments, and then perform a trial reduction using the same first set of instruments.

SUMMARY OF THE INVENTION

In one aspect of the invention, a system for preparing a long bone for a prosthetic, the long bone having a long axis comprises a distal instrument and a proximal instrument. The distal instrument is configured to remove bone from a distal portion of bone. The distal instrument has a bone removing portion configured to remove bone along the long axis of the long bone and a shaft extending from the bone removing portion along the long axis of the long bone. The proximal instrument is configured to overlie the shaft of the distal element within the long bone. The distal shaft guides the proximal instrument to prepare the proximal portion of the long bone after the distal instrument has prepared the distal portion of the long bone.

In another embodiment, the distal instrument is a reamer.

In yet another embodiment, the proximal instrument is a reamer.

Still another embodiment further comprises a trial neck body configured to attach to at least one of the distal instrument and the proximal instrument.

Alternatively, another embodiment further comprises a trial spacer configured to space the trial neck body from distal instrument.

Another embodiment includes the trial spacer and the trial neck body comprising a mating feature configured to adjustably orient a radial position.

In another embodiment, the mating feature is incrementally adjustable.

In yet another embodiment, the mating feature is lockable.

Alternatively, an embodiment further comprises a modular trial neck segment. The modular trial neck segment is configured to adjust at least one of an offset, version, or height of a trial component.

Another embodiment comprises a method for preparing a long bone having a long axis. The method includes removing bone from a distal portion of bone thereby leaving a cavity along the long axis of the long bone. The method also includes leaving a distal instrument within the long bone. Another step includes guiding a proximal instrument over a portion of the distal instrument to remove bone in a proximal portion of the bone.

Alternatively, the guiding step may comprise guiding the proximal instrument over a shaft aligned along the long axis of the bone.

In another embodiment, the removing step may comprise reaming the bone.

In yet another embodiment, a further step may include attaching a trial neck body to at least one of the distal instrument and the proximal instrument.

Another embodiment further comprises spacing the trial neck body from distal instrument.

Alternatively, another embodiment further comprises adjustably mating the trial neck body relative to the distal instrument to orient a radial position.

In another embodiment, the adjustably mating step is incrementally adjustable.

In yet another embodiment, the adjustably mating step may comprise locking the trial neck body to the distal instrument.

Another embodiment includes adjusting at least one of an offset, version, or height of a trial component by interchangeably using a plurality of multiple trial neck segments.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings.

DETAILED DESCRIPTION OF THE EMBODIMENTS

Figure 1:
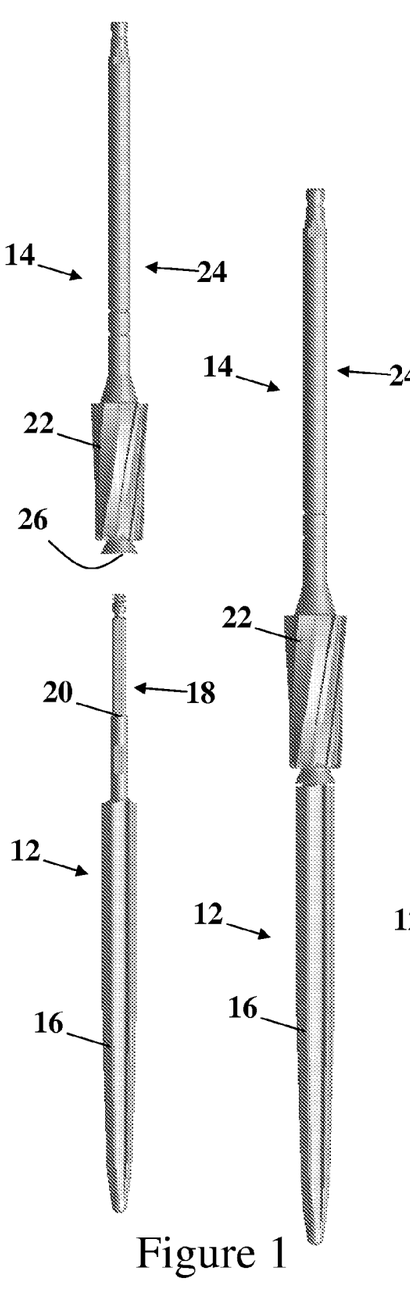
FIG. 1 is an exploded view and an assembled view of a reaming system according to an aspect of the invention.

Referring to the accompanying drawings in which like reference numbers indicate like elements, FIG. 1 is an exploded view and an assembled view of a reaming system 10 according to an aspect of the invention. The system 10 for removing bone material includes a distal cutting instrument 12 (e.g., a reamer) and a proximal cutting instrument 14. The distal reamer 12 includes at least one cutting edge 16, a shaft portion 18, and a mechanical stop feature 20. The proximal cutting instrument 14 includes at least one cutting edge 22, a shaft portion 24, a bore 26, and a mechanical stop feature within the bore 26. The bore 26 of the proximal cutting instrument 14 accepts the shaft 18 of the distal cutting instrument 12. The mechanical stops (either integral with the shaft portions or individual parts) of the two cutting instruments 12 and 14 abut to restrict axial movement further along the distal cutting instrument 12.

In one embodiment, each shaft portion 18 and 24 are configured to receive a drill. The drill may rotate the distal instrument 12 first to ream a distal portion of bone, then disconnect from the distal shaft portion 18, and reconnect to the proximal shaft portion 24 to ream a proximal bone portion. The cutting flutes 16 and 22 may be oriented to cut in the same direction or oriented to cut in opposite directions so that rotating the proximal instrument 14 would not further cut the distal portion of bone. The shafts 18 and 24 may also be isolated from one another so that rotating the proximal instrument 14 does not rotate the distal instrument 12.

The bore 26 of the proximal instrument 14 and the shaft 18 of the distal instrument 12 are axially aligned so that the cutting instruments 12 and 14 are coaxially aligned. The bore 26 may be formed to transmit torque to the distal instrument 12 or may be formed to rotate freely about the shaft 18. In such an embodiment, the distal shaft 18 serves to direct the proximal cutting instrument 14 on top of the distal cutting instrument 12.

While in this embodiment, the system 10 includes reamers, other embodiments may include impactors for impacting bone material. Such a system could include a distal impaction instrument and a proximal impaction instrument. The distal impaction instrument may include a smooth circular portion, a shaft portion, and a mechanical stop feature. The proximal impaction instrument may include a smooth circular portion, a shaft portion, a bore, and a mechanical stop feature. The bore of the proximal impaction instrument accepts the shaft of the distal impaction instrument, and the mechanical stop features of the two impaction instruments abut to restrict axial movement.

Figure 2:
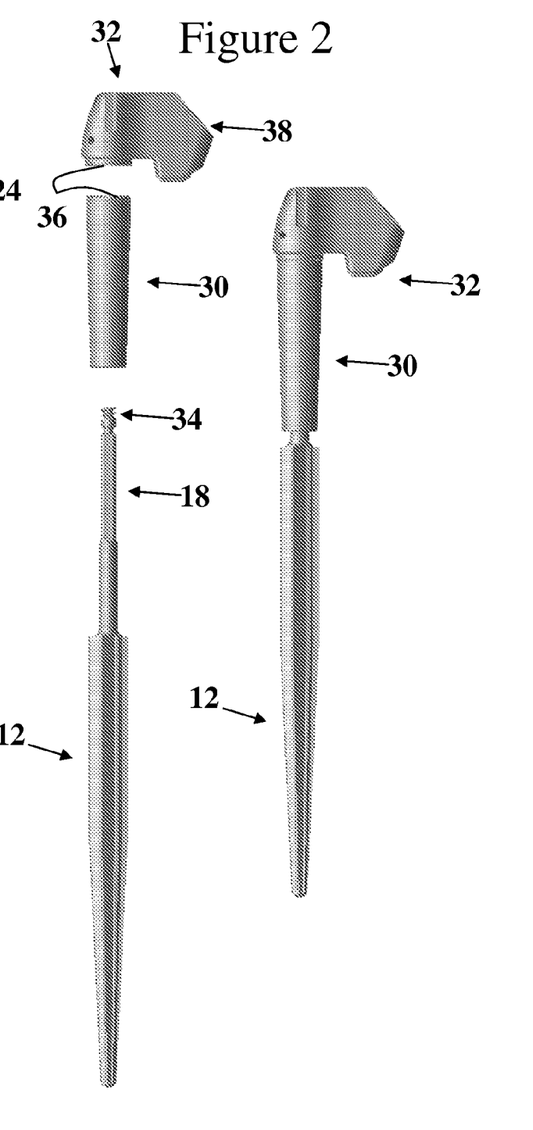
FIG. 2 is an exploded view and an assembled view of a trialing system according to an aspect of the invention.

FIG. 2 is an exploded view and an assembled view of a trialing system 28 according to an aspect of the invention. The trialing device 28 of the preferred embodiment generally comprises three components: a proximal trial spacer 30, a trial neck body assembly 32, and the distal cutting instrument 12. The proximal trial spacer 30 is primarily used to support the trial neck body assembly 32 on the distal reamer shaft 18 through a threaded portion 34 of the distal shaft 18, although this spacer 30 may not be necessary.

A trial modular neck segment (not shown) interfaces with the trial neck body assembly 38 through an interface surface 38. The neck segment is configured to support a head (e.g., femoral or humeral head), and may comprise a plurality of trial modular neck segments of different sizes and shapes to assess varying height, offset, version, and range of motion for the proposed implant. The trial modular neck segment may be configured to have a "stick fit" or press fit with the trial neck body assembly 32 (e.g., via use of a Morse taper on the interface surface 38), and the trial modular neck segment (and thus the interface surface 38) may or may not be reversible and may or may not be keyed.

The proximal trial spacer 30 and trial neck body assembly 32 may include a mating feature 36 such as a set of radially-extending, axially-disposed ridges and grooves which allow the orientation of the trial neck body assembly 32 to be adjusted incrementally with respect to both the proximal trial spacer 30 and the distal reamer 12. The trial neck body assembly 32 also may include a cut-out feature that allows a surgeon to mark neck orientation of the system onto bone with a surgical marker or bovie, in order to properly orient the final implant. As best seen in FIG. 2, the proximal trial spacer 30 has a frustoconical shape, a proximal end portion with a wide end and a distal end portion with a narrow end, the proximal end portion having the mating feature 36.

Figure 3:
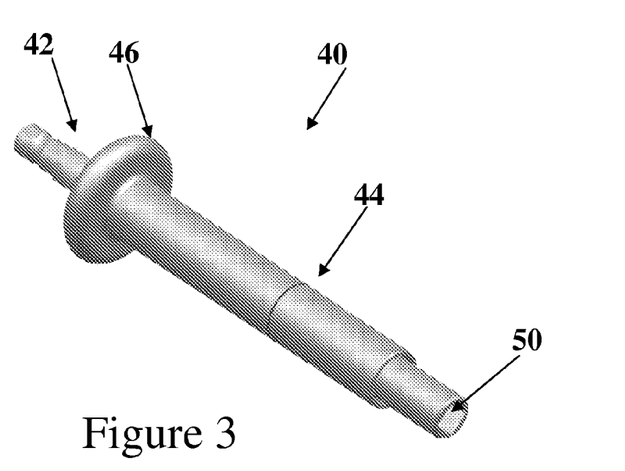
FIG. 3 is a view of a quick connect assembly for a reaming system.

FIG. 3 is a view of a quick connect assembly 40 for a reaming system. The quick connect assembly 40 includes an inner cylinder 42, an outer cylinder 44, a flange 46 and a drill connector 50. The inner cylinder 42 is axially slidable within the outer cylinder 44, and is biased so that the drill connector 50 is pressed away from the flange 46. The biasing means may be fixed axially to the outer cylinder 42, for example, through a pin (not shown) and extends through the outer and inner cylinders 42 and 44. The pin extends through the inner cylinder 42 within a slot. The slot also houses a spring which biases the drill connector 50 of the inner cylinder 42 axially away from the flange 46.

When the inner cylinder 42 is axially slid within the outer cylinder 44 (i.e., the drill connection 50 is depressed toward the flange 46), a pair of bearings may be slid out of the bottom of the quick connect assembly 40. The bearings extend radially outward from the quick connect assembly 40 to a distance greater than the inner diameter of the outer cylinder 44. With the bearings extending out from the inner cylinder 42, the quick connect assembly 40 is positioned to connect to the reamers 12 and 14.

The quick connect assembly 40 then may be used to quickly connect and disconnect the drill (attached to the quick connect assembly 40) from the distal reamer 12 and the proximal reamer 14. Thus, time lost to connecting, disconnecting and reconnecting the drill to the reamers is minimized This may reduce total surgical time, particularly when additional passes of the distal reamer 12 and proximal reamer 14 may be necessary.

Figure 4:
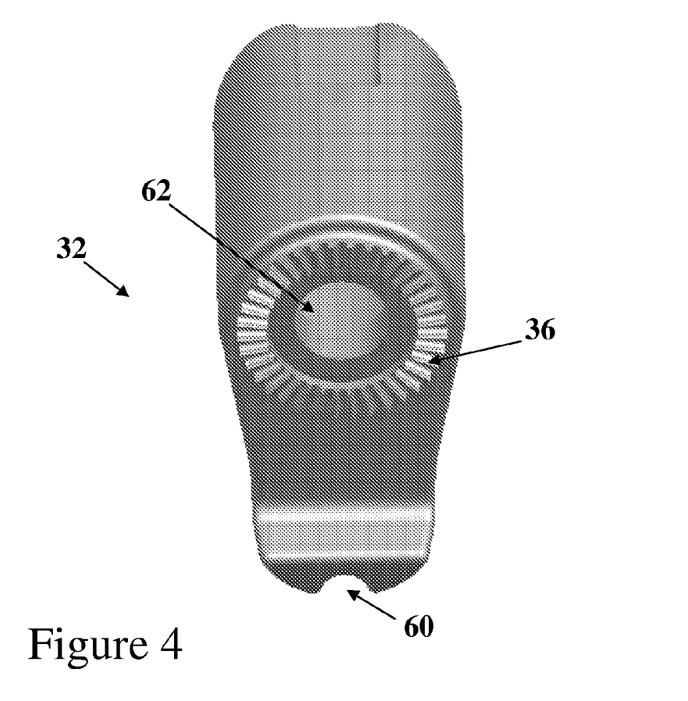
FIG. 4 is a view of a trial neck body.

FIG. 4 is a view of a trial neck body 32. The trial neck body assembly 32 may include the mating feature 36. The mating feature 36 may be a set of radially-extending, axially-disposed ridges and grooves which allow the orientation of the trial neck body assembly 32 to be adjusted incrementally with respect to both the proximal trial spacer 30 and the distal reamer 12. The trial neck body assembly 32 may be rotationally incremented to allow for proper orientation of the trial neck during trailing. The trial neck body assembly 32 also may include a cut-out feature 60 that allows a surgeon to mark neck orientation of the system onto bone with a surgical marker or bovie, in order to properly orient the final implant in the position that the trial neck body assembly 32 was oriented upon a final determined implant position. A neck bore 62 through the trial neck body assembly 32 allows the trial neck body assembly 32 to be fixed to the threaded portion 34 of the distal reamer 12 by a locking nut. The connection between the trial neck body assembly 32 and the distal reamer 12 compresses the mating surfaces 36 to lock the trial in place. While this embodiment includes a locking nut and radially extending, axially disposed ridges, other devices that provisionally lock the trial neck body assembly 32 in place would achieve the same results as the current embodiment.

Figure 5:
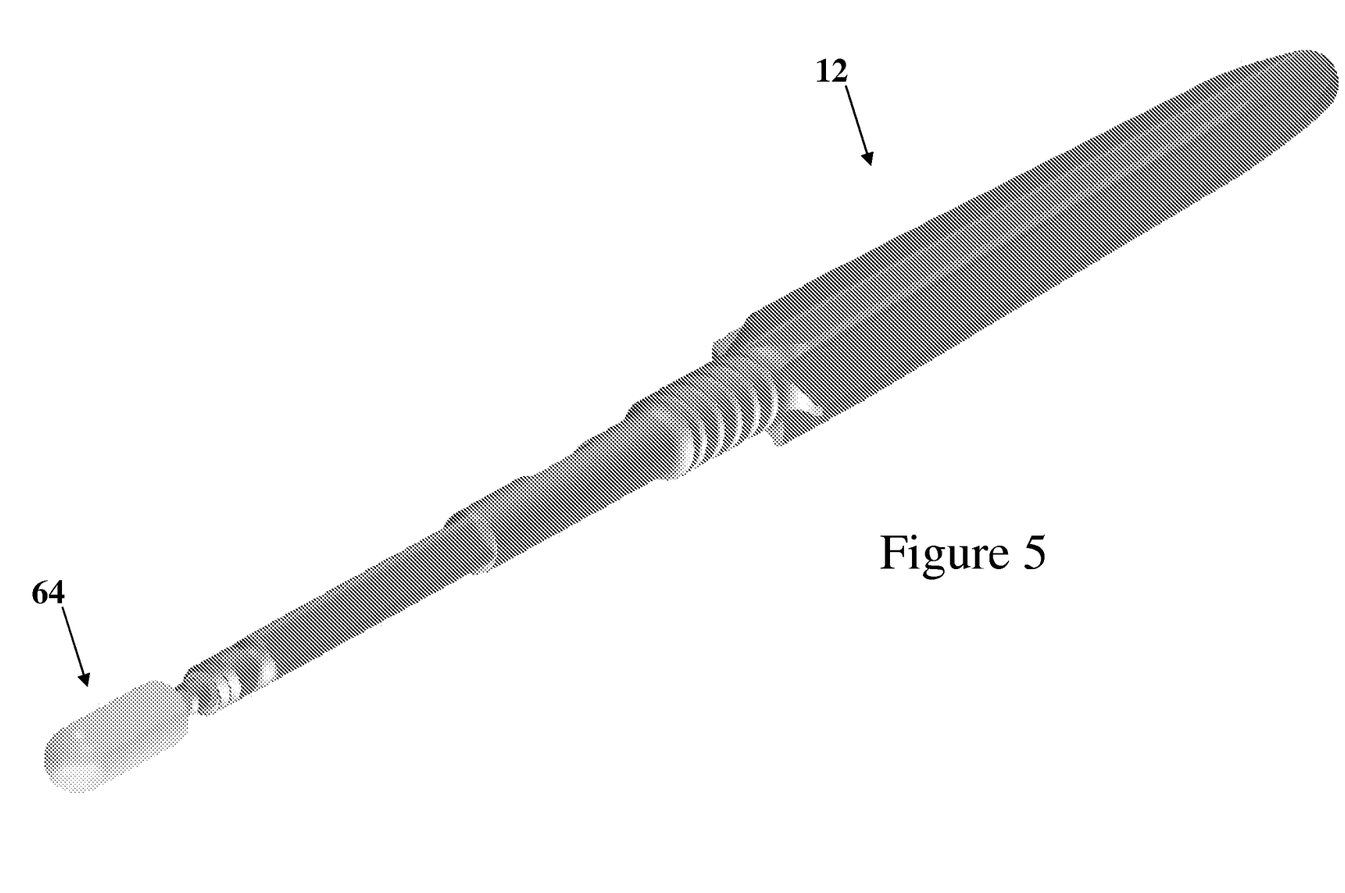
FIG. 5 is a view of a distal reamer with a cap.

FIG. 5 is a view of the distal reamer 12 with a cap 64. The cap 64 serves as a protector of the threaded portion 34 of the reamer. The cap 64 may protect the threaded portion from damage as the drill rotates the distal reamer 12.

Figure 6:
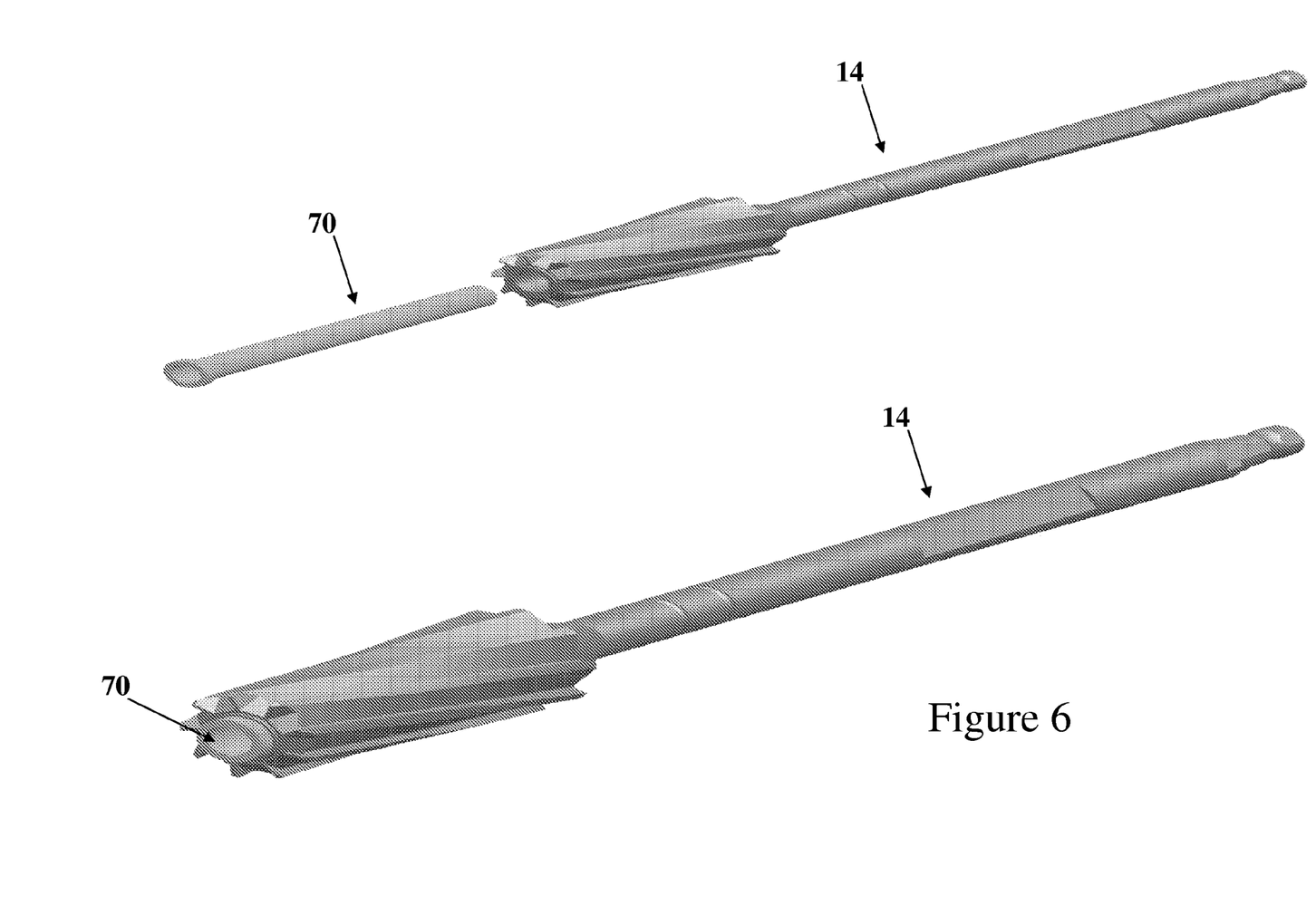
FIG. 6 is an exploded view and an assembled view of an insert and a proximal reamer.

FIG. 6 is a view of an insert 70 and the proximal reamer 14. The insert 70 may slide into the bore 26 of the distal reamer 14. The insert 70 may protect the distal reamer 14 and the proximal reamer 12 from friction, which could bind the reamers 12 and 14, or could increase chatter between the reamers 12 and 14. Additionally, chatter could cause the distal reamer to continue to cut through distal bone. Such additional movement may cause poor distal fixation of the implant.

Figure 7:
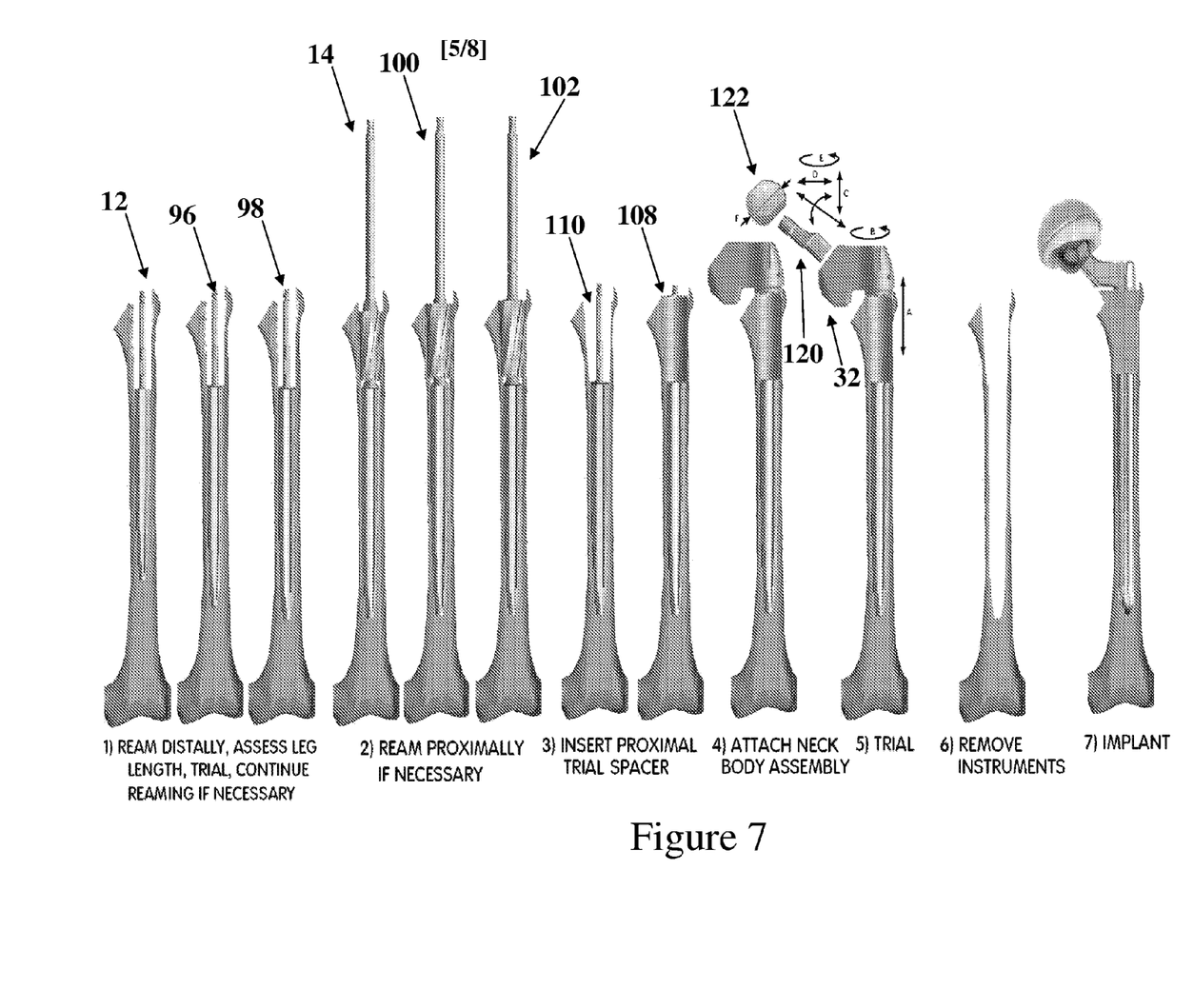
FIG. 7 is a view of steps for preparing a femur and trialing the femur.

FIG. 7 is a view of steps for preparing a femur 80 and trialing the femur 80. A femoral neck osteotomy and acetabular preparation (not shown) are first performed. The femoral canal is prepared for reaming. A quick connect device may be attached to the appropriately sized distal reamer, or the reamer may be directly attached to a drill. Reaming begins with a distal reamer that is 4-6 mm smaller than the templated size. At all times, the reaming should be done so that the reamer has little or no resistance, which may minimize heat in the bone. The reamers may use depth mark either on the reamer or on the quick connect instrument corresponding to the neutral head center of the prosthesis, to gauge the appropriate reaming depth. The depth marks may reference the greater trochanter. The femoral canal is sequentially expanded using the distal reamers. For example, the reamers may change size by 0.5 mm increments until the last reamer matches the selected implant size. The final reamer size may need to be adjusted based on bone quality, anatomy and surgeon preference.

Distal reamer depth may also change. The distal reamer 12 may be the shortest reamer. A mid size distal reamer 96 may allow for more distal fixation while a long reamer 98 may allow for deep distal reaming. The diameter size of the reamers may also change according to bone quality, anatomy and surgeon preference. The choice for length will also depend on bone quality, anatomy and surgeon preference both distally and proximally.

After distal reaming is complete, the final distal reamer is left in-situ. A starter reamer over the top of the final distal reamer reams the proximal femur. The starter reamer may remove any trochanteric bone that may impede the proximal reaming process. The starter reamer has a mechanical axial stop that will abut the distal reamer and prevent excess bone removal.

Proximal reamers 14, 100 and 102 prepare the femur for the modular sleeve implant. These reamers are sized according to cone size and distal diameter. First the reamer with the smallest cone size that corresponds with the distal diameter of the stem reams over the top of the distal reamer (for example, for a size 13, select a 13S proximal reamer, first.) Progressively, reamers of larger diameters and cone sizes are used to ream until the desired fit is achieved. The length of the distal reamer corresponds to the length of the sleeve and may effect the leg length (A) of the trial.

After the proximal femur is reamed, then a trial spacer 108 is placed within the proximal femur recess 110. As best seen in FIG. 7, the trial spacer 108 matches in shape to the bone removed in the proximal femur recess 110. The trial neck body assembly 32 is attached to the distal reamer. A neck segment 120 and head 122 are assembled to the trial to reduce the hip and assess leg length and joint tension/stability. By varying the trial neck segment 120, neck offset (D) and neck height (C) may be adjusted by selecting a different trial modular neck segment 120. Neck version (E) may be adjusted by either using a trial modular neck segment having a built-in specified version angle, or by unscrewing a trial neck body assembly screw and radially orienting the trial neck body assembly with the optimum version (B). Desired version may be marked on the bone with a bovie or skin marker with respect to the orientation marker on the trial neck body assembly. The trial instruments are removed from the bone.

The distal stem and proximal sleeve/body are assembled. The stem and sleeve/body implant are impacted into the prepared canal, and oriented referencing any marks made with the skin marker or bovie. Select modular neck segment and head according to the trial components used in the trial reduction procedure previously. The modular neck segment is impacted onto the body and the head is assembled. The hip is reduced to ensure correct stability and joint tension.

While this procedure has been described with respect to a primary hip system, a revision hip system would proceed similarly after the failed primary system has been removed. This implant system may be more beneficial in a revision as the modular choices of the implant allows for accommodating different bone deficiencies. It should be appreciated that there could obviously be extra steps involved with reconstruction of the femur comprising the use of cables, struts, and augments (metal, active, and/or bioabsorbable) etc. especially if there is an ETO (extended trochanteric osteotomy) involved.

Alternative embodiments of the present invention may include reamers having some of the features above in combination with any or all of the following features. The top of the distal reamer shaft may act as the mechanical stop feature to restrict axial movement of the proximal reamer when reaming atop the distal reamer shaft. The mechanical stop feature may broadly comprise any one of a shelf, ledge, step, ring, flange, plate, end portion, male/female connection, or any other feature which may prevent further axial movement.

The distal and proximal reamers may connect directly to the hospital's standard powered drill/reamer device with or without the need for the quick connect adapter device of the present invention. The distal and proximal reamers may connect directly to a non-powered T-handle with or without the need for the quick connect adapter base of the present invention. The top of the bore of the proximal reamer may act as the mechanical stop feature to restrict axial movement of the proximal reamer when reaming atop the distal reamer shaft. The distal end portion of the proximal reamer may act as the mechanical stop feature which restricts axial movement of the proximal reamer when reaming atop the distal reamer shaft. The proximal reamer may or may not have a depth mark or other orientation marks corresponding with references to bony or other anatomy. The proximal trial spacer may or may not have a depth mark or other orientation marks corresponding with references to bony or other anatomy. The trial neck body assembly may or may not have a depth mark or other orientation marks corresponding with references to bony or other anatomy.

Figure 8:
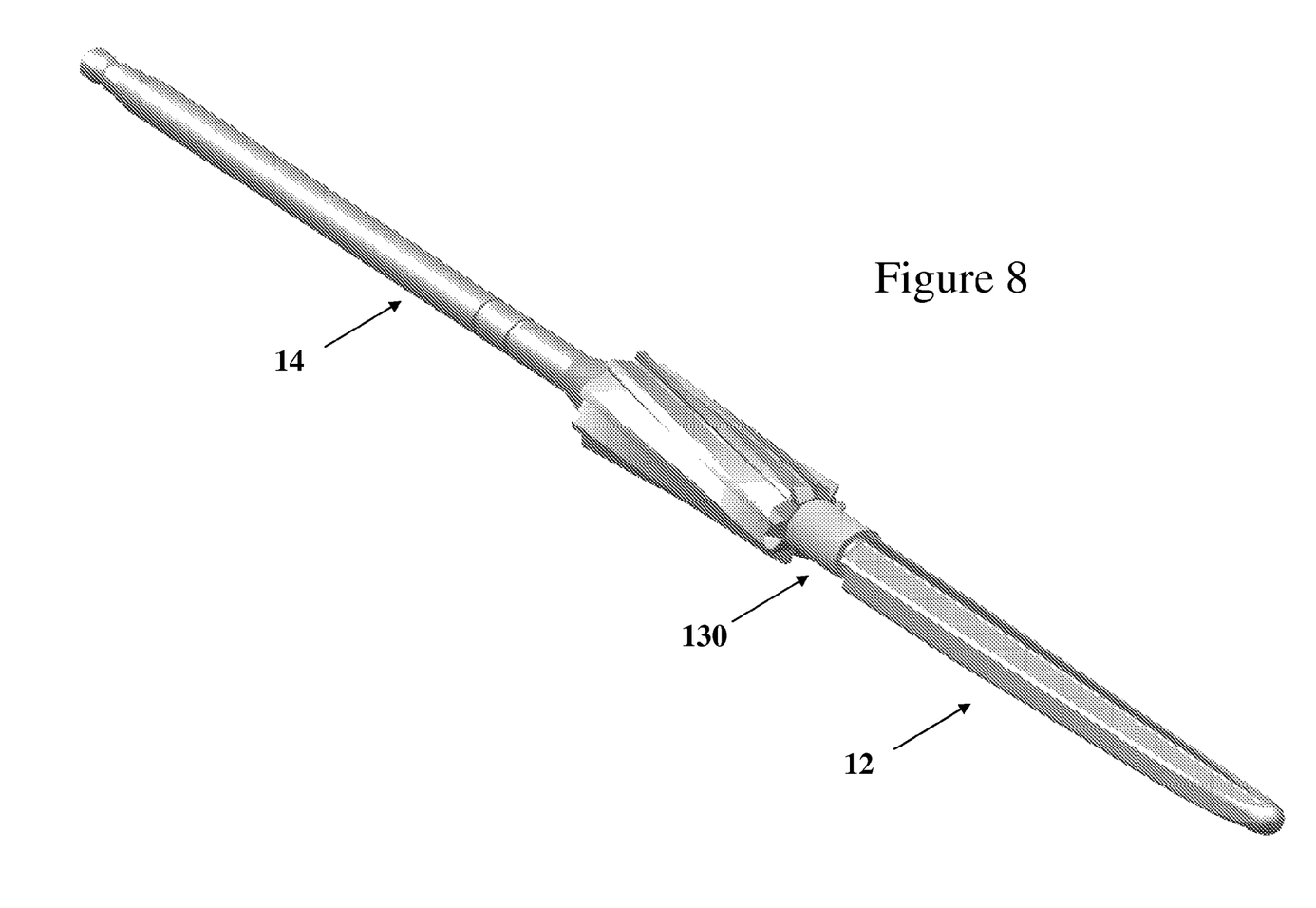
FIG. 8 is a view of a reaming system including a spacer.

FIG. 8 is a view of a reaming system including a spacer 130. The spacer 130 may space the proximal reamer 14 from the distal reamer 12. One or more spacer components 130 may fit between the distal and proximal reamers. The spacer components 130 may vary in size, length, and geometry, although it is preferred to have a single length spacer component.

Figure 9:
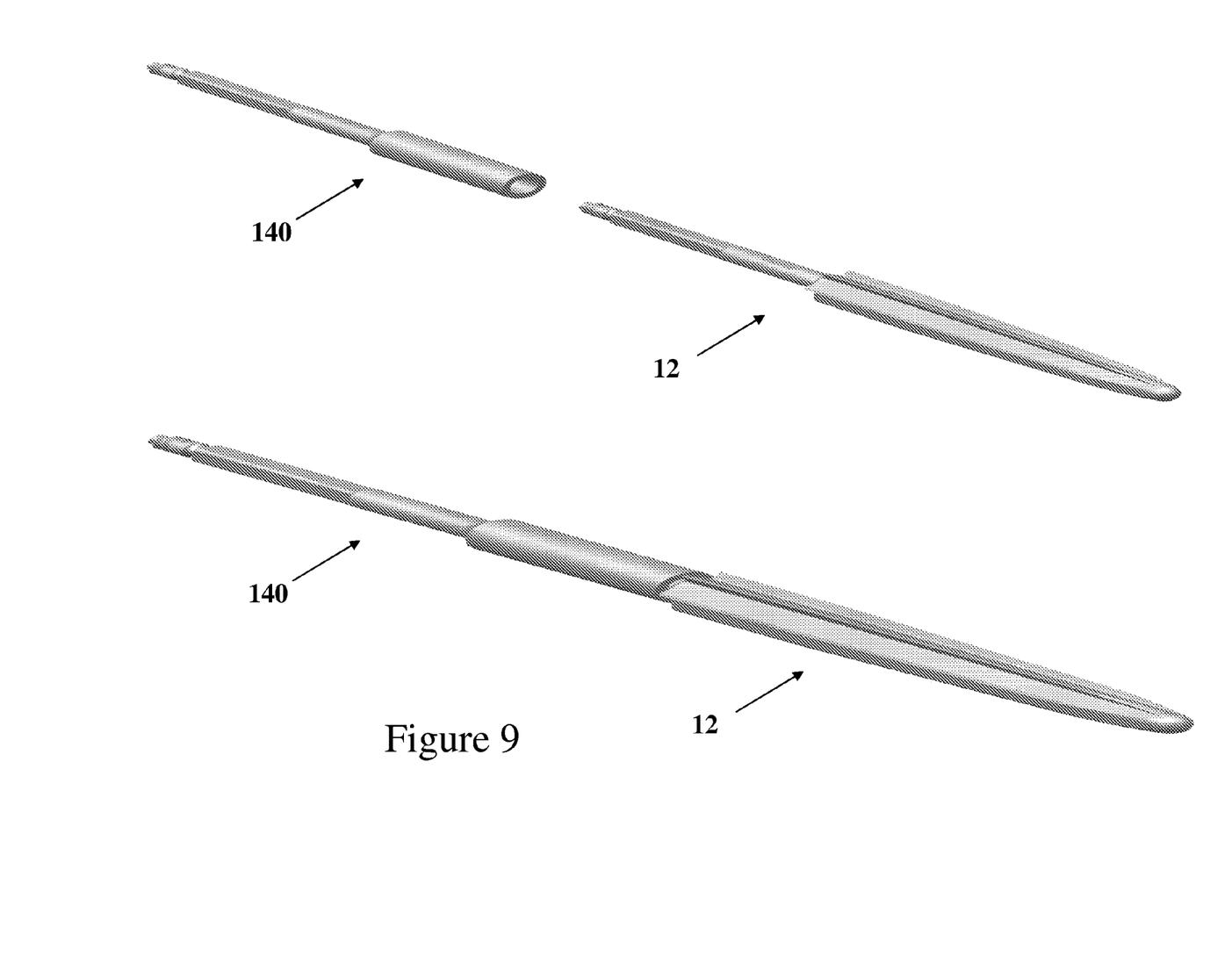
FIG. 9 is an exploded view and an assembled view of a distal reamer and an extender.

FIG. 9 is an exploded view and an assembled view of a distal reamer 12 and an extender 140. The removable distal reamer extension may fit proximally atop (as shown) or distally below (not shown) the distal reamer to allow the distal reamer to ream further into the femoral canal. The reamer and extension may be formed as a single integral piece.

Figure 10:
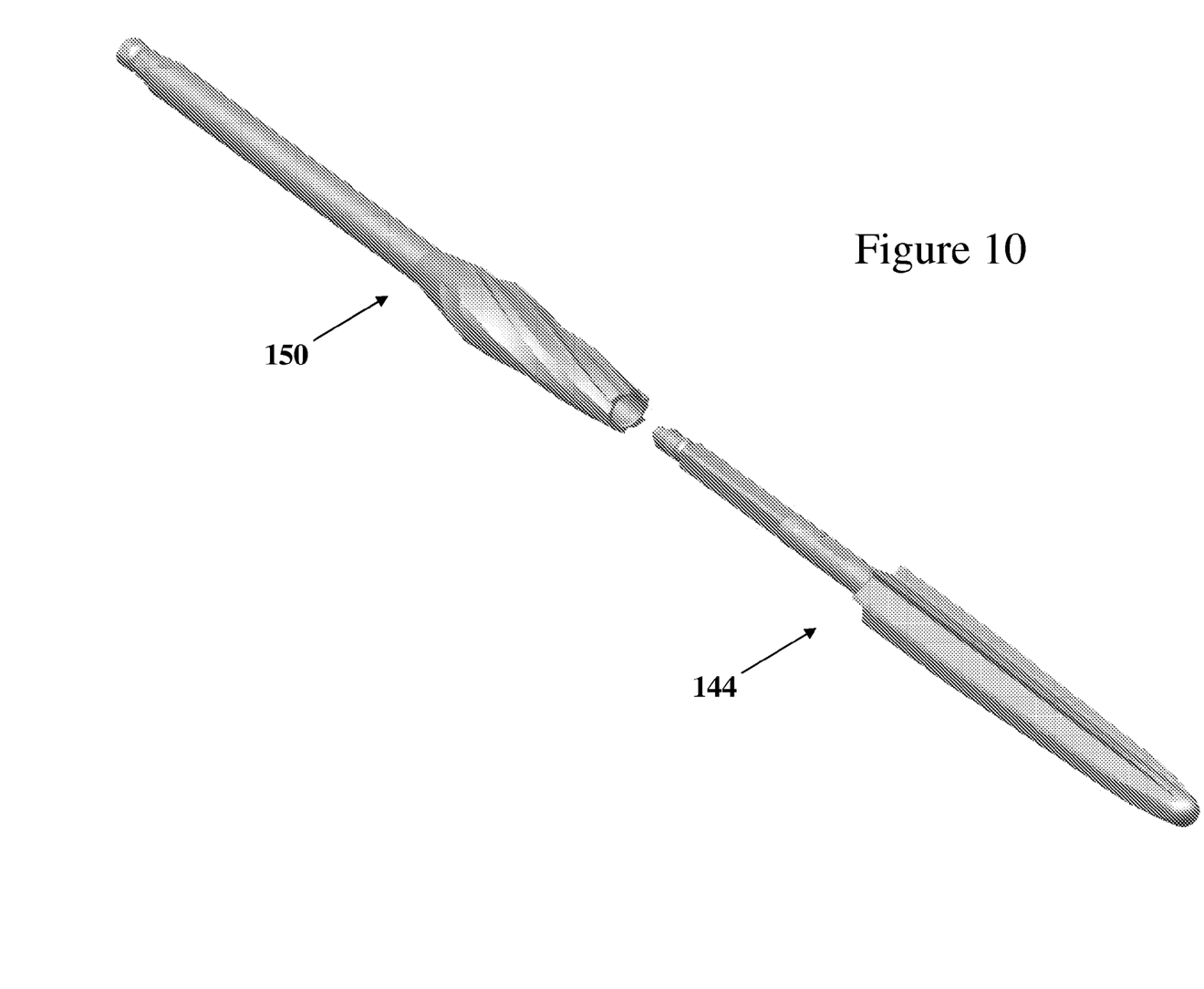
FIG. 10 is an exploded view of a distal reamer and a starter proximal reamer.

FIG. 10 is an exploded view of a distal reamer 144 and a starter proximal reamer 150. The additional starter reamer component may be utilized to open the canal prior to the proximal reamer step. This "starter" reamer may fit atop the distal reamer component. Alternatively, if there is significant proximal bone loss, proximal reaming with either the proximal reamer or starter reamer may be omitted.

An alternative embodiment of the present invention comprises making two of the at least three components (distal stem, proximal trial spacer, and trial neck body assembly) of the preferred embodiment integral with each other. For example, the proximal trial spacer and trial neck body assembly may be formed as a single integral piece and may come available several available sizes and shapes. Alternatively, the trial neck body assembly and the trial modular neck segments (not shown) may be formed as a single integral piece. In another embodiment, the distal reamer extension disclosed above may be made integral with the distal reamer. Other embodiments may include the protective sleeve disclosed above and the proximal reamer may be made integral with each other. That is, the protective sleeve may be formed of a similar or dissimilar material and pressed into the proximal reamer, or the protective sleeve geometries may be "built into" the proximal reamer and formed as a single integral piece.

The trial modular neck segments used with the present invention may be designed such that an array of trial modular neck segments can address various neck lengths, heights, offsets, and versions, such to replicate the final implant.

The proximal trial spacer may abut the reamed bone created by the proximal reamer. There may be a plurality of sizes of proximal trial spacers such that a single proximal trial can be selected to fit the reamed area of several differently-sized proximal reamers. The proximal trial spacer may be made integral with the distal reamer if proximal reaming is not necessary.

The proximal trial spacer, trial neck body assembly, and trial modular neck segment may be attached prior to reaming for the proximal implant. In other words, proximal reaming may be done after a first trial reduction and leg length assessment is completed.

In yet another embodiment, a system of the present invention comprises at least two differently-sized distal reamers, at least two differently-sized proximal reamers, and a proximal trial spacer. The proximal trial spacer may be one size fits all, or a plurality of sizes and geometries of proximal trial spacer components may be provided. In addition, the system may further comprise one or more trial neck body assemblies, and/or one or more trial modular neck segments. The trial modular neck segments may be keyed such that they may be capable of universal or selective use between revision product lines and/or primary product lines, or use to within a specified range of stem sizes within a particular product line.

Moreover in yet another embodiment, the present invention may be used in knee arthroplasty to bore holes in the tibia or femur. For example, in a knee revision, a distal intramedullary tibial reamer may be used to bore a hole and fix itself into the bone. A proximal intramedullary reamer may then be placed over the distal intramedullary tibial reamer to clean up the proximal portion of the tibia or enlarge the hole more proximally for fins or other stem features requiring a larger diameter bore. A trial tibial tray/insert component may then be attached to said distal intramedullary reamer with or without the use of a supporting proximal trial spacer between the distal intramedullary reamer and said trial tibial tray/insert component. Trial reduction is performed, and then a best fit implant size and geometry is selected. The distal intramedullary reamer (and supporting proximal trial spacer if applicable) is then removed, and then the implant is installed. Using the present invention, there is no need to insert a trial tibial tray into the tibia, since all trialing is done off of the distal intramedullary reamer left in-situ.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method for preparing a long bone having a long axis, comprising the steps of:
   selecting a distal cutting instrument having a proximal end, a distal end having at least one cutting edge, and a shaft with a mechanical stop feature;
   reaming using the distal cutting instrument along a longitudinal axis to remove bone from a distal portion of bone thereby leaving a cavity along the long axis of the long bone;
   leaving the distal cutting instrument within the long bone;

selecting a proximal cutting instrument having at least one cutting edge, a shaft portion, and a bore;

guiding the bore of the proximal instrument over the shaft portion of the distal cutting instrument such that the proximal cutting instrument is co-axially aligned with the distal cutting instrument;

reaming using the proximal cutting instrument along the longitudinal axis until the bore abuts the mechanical stop feature to remove bone in a proximal portion of the bone;

removing the proximal cutting instrument;

providing a proximal trial spacer with a frustoconical shape that matches the removed bone in the proximal portion, the proximal trial spacer having a proximal end portion with a wide end and a distal end portion with a narrow end, the proximal end portion having a mating feature;

guiding the proximal trial spacer over the shaft portion of the distal cutting instrument;

attaching a trial neck body having a mating feature to the distal cutting instrument;

adjustably mating the trial neck body mating feature to the mating feature of the proximal trial spacer and relative to the distal cutting instrument to orient a radial position; and locking the trial neck body to the distal cutting instrument using a locking mechanism.

2. The method of claim 1, further comprising the step of adjusting at least one of an offset, version, or height of a trial component by interchangeably using a plurality of multiple trial neck segments.

3. The method of claim 1, further comprising the step of removing the distal cutting instrument, the proximal cutting instrument, and the trial neck body.

4. The method of claim 1, further comprising the step of implanting a hip implant.

5. The method of claim 1, wherein the trial neck body includes an interface surface.

6. The method of claim 1, wherein the trial neck body includes a cut out feature.

7. The method of claim 1, wherein the step of adjustably mating the trial neck body step comprises incremental rotation of the trial neck body.

8. The method of claim 1, further comprising providing a spacer to space the proximal cutting instrument from the distal cutting instrument.

9. The method of claim 1, further comprising attaching an extender to the distal cutting instrument.

10. The method of claim 1, wherein the proximal trial spacer abuts reamed bone created by the proximal cutting instrument.

11. The method of claim 1, wherein the proximal trial spacer is integral with the distal cutting instrument.

12. The method of claim 1, wherein the step of reaming with the proximal cutting instrument is performed after a trial reduction and leg length assessment.

13. The method of claim 1, wherein there are at least two distal cutting instruments, at least two proximal cutting instruments, and at least one proximal trial spacer.

14. The method of claim 1, wherein the mating feature of the proximal trial spacer and the mating feature of the trial neck body each comprise radially-extending, axially-disposed ridges and grooves.

15. The method of claim 1, wherein the mechanical stop feature is integral with the shaft portion of the distal cutting instrument.

16. The method of claim 1, further comprising the step of selecting the proximal trial spacer.

17. The method of claim 16, wherein the proximal trial spacer is selected according to size.

18. A method for preparing a long bone having a long axis comprising the steps of:

selecting a distal reamer having a proximal end, a distal end having at least one cutting edge, and a shaft with a mechanical stop feature;

reaming using the distal reamer along a longitudinal axis to remove bone from a distal portion of bone thereby leaving a cavity along the long axis of the long bone;

leaving the distal reamer within the cavity, the distal reamer having the shaft aligned along the long axis of the bone;

selecting a proximal reamer having at least one cutting edge, a shaft portion, and a bore;

guiding the bore of the proximal reamer over a portion of the shaft of the distal reamer such that proximal reamer is co-axially aligned with the distal reamer;

reaming using the proximal reamer along the longitudinal axis to remove bone in a proximal portion of the bone;

restricting an axial depth of the bone removed from the proximal portion using the engagement of the bore with the mechanical stop feature;

providing a proximal trial spacer with a shape that matches the removed bone in the proximal portion, the proximal trial spacer having a proximal end portion and a distal end portion;

guiding the proximal trial spacer over the shaft portion of the distal cutting instrument to space a trial neck body from the at least one cutting edge of the distal reamer;

attaching the trial neck body to the distal reamer;

adjustably mating the trial neck body to the proximal end portion of the proximal trial spacer and relative to the distal reamer to orient a radial position; and locking the trial neck body to the proximal end of the distal reamer.

19. The method of claim 18, further comprising the step of removing the distal reamer, the proximal reamer, and the trial neck body.

20. The method of claim 18, further comprising the step of implanting a hip implant.

21. The method of claim 18, further comprising the step of adjusting at least one of an offset, version, or height of a trial component by interchangeably using a plurality of multiple trial neck segments.

22. The method according to claim 18, further comprising removing the proximal reamer.

23. The method of claim 18, wherein the trial neck body includes an interface surface.

24. The method of claim 18, wherein the trial neck body includes a cut out feature.

25. The method of claim 18, wherein the adjustably mating step comprises incremental rotation of the trial neck body.

26. The method of claim 18, further comprising providing a spacer to space the proximal reamer from the distal reamer.

27. The method of claim 18, further comprising attaching an extender to the distal reamer.

28. The method of claim 18, wherein the proximal trial spacer abuts reamed bone created by the proximal reamer.

29. The method of claim 18, wherein the step of reaming using the proximal reamer is performed after a trial reduction and leg length assessment.

30. The method of claim 18, wherein the adjustably mating the trial neck body step comprises connecting a mating feature of the proximal trial spacer with a mating feature of the trial neck body, and wherein each mating feature comprises radially-extending, axially-disposed ridges and grooves.

31. The method of claim 18, wherein the mechanical stop feature is integral with the shaft of the distal reamer.

32. The method according to claim 18, wherein the proximal trial spacer has a frustoconical shape with the proximal end portion having a wide end and the distal end portion having a narrow end.

33. The method of claim 32, wherein the proximal trial spacer is selected according to size.

34. The method of claim 32, wherein the proximal trial spacer is integral with the distal reamer.

35. The method of claim 32, wherein there are at least two distal reamers, at least two proximal reamers, and at least one proximal trial spacer.

36. A method for preparing a long bone having a long axis comprising the steps of:
    selecting a distal instrument having a proximal end, a distal end having at least one cutting edge, and a shaft with a mechanical stop feature;
    removing bone along a longitudinal axis using the distal instrument thereby leaving a cavity along the long axis of the long bone;
    leaving the distal instrument within the cavity, the distal instrument having the shaft aligned along the long axis of the bone;
    selecting a proximal instrument having at least one cutting edge, a shaft portion, and a bore;
    placing the proximal instrument over a portion of the distal instrument such that the bore of the proximal instrument receives a portion of the shaft of the distal instrument and is coaxially aligned with the distal instrument;
    removing bone along the longitudinal axis using the proximal instrument;
    restricting an axial depth of the bone removed from the proximal portion by engaging the bore with the mechanical stop feature;
    providing a proximal trial spacer with a shape that matches the removed bone in the proximal portion, the proximal trial spacer having a proximal end portion and a distal end portion;
    guiding the proximal trial spacer over the shaft portion of the distal cutting instrument to space a trial neck body from the at least one cutting edge of the distal instrument;
    adjustably mating the trial neck body to the proximal end portion of the proximal trial spacer and relative to the distal instrument to orient a radial position; and
    locking the trial neck body to the distal instrument.

37. The method of claim 36, further comprising the step of removing the distal instrument, the proximal instrument, and the trial neck body.

38. The method of claim 36, further comprising the step of implanting a hip implant.

39. The method of claim 36, further comprising the step of adjusting at least one of an offset, version, or height of a trial component by interchangeably using a plurality of multiple trial neck segments.

40. The method according to claim 36, further comprising removing the proximal reamer.

41. The method of claim 36, wherein the trial neck body includes an interface surface.

42. The method of claim 36, wherein the trial neck body includes a cut out feature.

43. The method of claim 36, wherein the step of adjustably mating the trial neck body comprises incremental rotation of the trial neck body.

44. The method of claim 36, further comprising providing a spacer to space the proximal instrument from the distal instrument.

45. The method of claim 36, further comprising attaching an extender to the distal instrument.

46. The method of claim 36, wherein the step of removing bone with the proximal instrument is performed after a trial reduction and leg length assessment.

47. The method of claim 36, wherein the adjustably mating the trial neck body step comprises connecting a mating feature of the proximal trial spacer with a mating feature of the trial neck body, and wherein each mating feature comprises radially-extending, axially-disposal ridges and grooves.

48. The method of claim 36, wherein the mechanical stop feature is integral with the shaft of the distal instrument.

49. The method according to claim 36, wherein the proximal trial spacer has a frustoconical shape with the proximal end portion having a wide end and the distal end portion having a narrow end.

50. The method of claim 49, wherein the proximal trial spacer is selected according to size.

51. The method of claim 49, wherein the proximal trial spacer abuts reamed bone created by the proximal instrument.

52. The method of claim 49, wherein the proximal trial spacer is integral with the distal instrument.

53. The method of claim 49, wherein there are at least two distal instruments, at least two proximal instruments, and at least one proximal trial spacer.

* * * * *